(12) United States Patent
Bristow

(10) Patent No.: US 7,833,735 B2
(45) Date of Patent: Nov. 16, 2010

(54) DETECTION OF SURFACE-ASSOCIATED HUMAN LEUKOCYTE ELASTASE

(75) Inventor: Cynthia L. Bristow, New York, NY (US)

(73) Assignee: Ronald Winston

( * ) Notice: Subject to any disclaimer, the term of this patent is extended or adjusted under 35 U.S.C. 154(b) by 0 days.

(21) Appl. No.: 11/452,028

(22) Filed: Jun. 13, 2006

(65) Prior Publication Data

US 2006/0234312 A1  Oct. 19, 2006

Related U.S. Application Data

(63) Continuation-in-part of application No. 11/062,982, filed on Feb. 22, 2005, now abandoned, which is a continuation of application No. 09/899,498, filed on Jul. 5, 2001, now Pat. No. 6,858,400.

(60) Provisional application No. 60/216,232, filed on Jul. 5, 2000.

(51) Int. Cl.
*G01N 33/573* (2006.01)
*G01N 33/574* (2006.01)

(52) U.S. Cl. ............... 435/7.23; 435/7.24; 435/7.4; 435/962

(58) Field of Classification Search ............ None
See application file for complete search history.

(56) References Cited

U.S. PATENT DOCUMENTS 6,858,400 B2 * 2/2005 Bristow ............... 435/7.24

* cited by examiner

*Primary Examiner*—David A. Saunders
(74) *Attorney, Agent, or Firm*—Edwards Angell Palmer & Dodge LLP; Peter C. Schechter

(57) ABSTRACT

In order to accurately and reliably quantitate HLE on the plasma membranes of the lymphocytes and mononuclear phagocytes, a test sample containing the lymphocytes and mononuclear phagocytes is initially treated with a first antiserum specific for CD4 receptors on the plasma membrane or with a second antiserum specific for chemokine receptors on the plasma membrane. Once the CD4 or chemokine receptors have been rendered non-reactive (competitive) relative to the HLE receptors (also "binding sites") on the plasma membrane, the test sample is contacted with an immunoreagent specific for interaction with one or more of the HLE receptors on the plasma membranes of the lymphocytes and mononuclear phagocytes. The immunoreagent forms a complex with the HLE binding sites and produces a characteristic physical change in the lymphocytes and mononuclear phagocytes that can be monitored by anyone of a number of standard techniques, (e.g., confocal laser scanning microscopy and flow cytometry).

7 Claims, No Drawings

DETECTION OF SURFACE-ASSOCIATED HUMAN LEUKOCYTE ELASTASE

RELATED APPLICATIONS

This application is a Continuation-In-Part of application Ser. No. 11/062,982, filed Feb. 22, 2005 now abandoned which in turn is a continuation of Ser. No. 09/899,498, filed Jul. 5, 2001, now U.S. Pat. No. 6,858,400, which claims the filing date of Provisional Application Ser. No. 60/216,232, filed Jul. 5, 2000.

BACKGROUND OF THE INVENTION

1. Field of the Invention

This invention relates to a method. More specifically, this invention relates to a method of analysis, and to a test kit for performance of such analysis. The preferred method of analysis of this invention involves the use of a diagnostic test kit specific for the quantitative determination of Human Leukocyte Elastase (HLE) on the plasma membranes of lymphocytes and mononuclear phagocytes as means of monitoring pathologic response of such cells to various disease states.

2. Description of the Prior Art

It is known that Human Leukocyte Elastase (HLE) is co-localized with CD4 and chemokine receptors on the plasma membrane of lymphocytes and mononuclear phagocytes. Human lymphocytes, mononuclear phagocytes, and polymorphonuclear cells derive from lineage-committed pluripotent stem cells along discrete pathways determined in bone marrow. HLE is localized on the plasma membrane early in ontogeny and is granule-localized later in ontogeny suggesting that HLE is an early differentiation marker (Borregaard and Cowland, *Granules Of The Human Neutrophilic Polymorphonuclear Leukocyte*, Blood, Vol. 89:3503-3521 (1997).

The primary function of cell-surface HLE appears to involve cell motility, and recent evidence suggests modulation of cell-surface HLE dramatically influences cellular response. Although plasma membrane-associated HLE has been previously shown to produce membrane-associated cellular response factors, detection of cell-surface HLE density has not heretofore been recognized as a reliable barometer of, nor utilized to monitor, corresponding pathologic responses, such as the onset or progression of an HIV infection. More specifically, immunochemical interaction of antibodies specific with markers characteristic of cell-surface HLE have been generally unreliable as a measurement of cell-surface density of HLE. The reason for such lack of correlation has up to now been unknown. It has recently been observed that when cells from healthy volunteers are infected in vitro, HIV production is correlated with the cell surface density of HLE, but not to HIV receptors CD4, CXCR4, nor CCR5, (Bristow, C. L., Clin. Diagn. Lab. Immunol., Vol. 8, September 2001.). These recent data indicate that HIV infection is facilitated by co-patching with CD4, CXCR4, and HLE on extensions of the plasma membrane. Accordingly, a primary function for HLE in CD4-related events, appears to include HIV entry and augmentation of immune response.

The conventional method for determining the presence or progression, of a pathologic disease state, generally involves monitoring of certain analytes in specific biological fluids for the presence or absence of the pathogen, or a protein (e.g. antibody) produced by the individuals immune system in response to the presence of the pathogen. Notwithstanding, the availability of such analysis, the extent or progression of a pathologic disease state is not generally ascertainable by such techniques because of the lack of direct quantitation in change in concentration of the pathogens in such assays. Where, as in the case of an HIV infection, the extent of such infection is determined indirectly by analysis of the blood samples for the presence of cells critical to immune response. This type of analytical protocol is of little or any value in the monitoring of seropostive HIV positive individuals who do not express the classical AIDS symptoms, nor is it of value in subtle adjustment in applied therapies in the containment or treatment to prevent the progression of AIDS. Accordingly, there continues to exist a need for a simple and effective diagnostic test to quantitatively measure pathologic disease states, such as an HIV infection, including changes in disease progression, to assist in the prescription of an appropriate therapy, or in the adjustment in the dosage of such therapy. Such diagnostic test, to be effective, should be based upon changes in some parameter, in the basal level of an analyte, which is sensitive to and directly implicated by the pathologic changes associated with different disease states.

OBJECTS OF THE INVENTION

It is the above as well as related object of this invention to remedy the above as well as related deficiencies in the prior art.

More specifically, it is the principle object of this invention to provide a non-invasive diagnostic test for monitoring of disease progression and pathologic phenomena that correlated, either directly or inversely, with Human Leukocyte Elastase (HLE) in plasma membranes.

It is another object of this invention to provide a non-invasive diagnostic test for monitoring the progression of an HIV infection by monitoring and quantitation of plasma membrane Human Leukocyte Elastase (HLE) in seropositive HIV individuals that experience an Aids Related Condition (also herein "ARC Individuals"); and, individuals that have Acquire Immune Deficiency Syndrome (AIDS) (also "AIDS Individuals").

It is yet another object of this invention to provide a non-invasive diagnostic test kit suitable for monitoring of disease progression and pathologic phenomena that correlated, either directly or inversely, with plasma membrane Human Leukocyte Elastase (HLE).

SUMMARY OF THE INVENTION

The invention is directed to a method for monitoring of disease progression and pathologic phenomena that correlate with surface density of Human Leukocyte Elastase (HLE) associated with plasma membranes. More specifically, plasma membrane concentration of HLE dramatically influences cellular response to pathologic states resulting from microbial organisms, transplantation, autoimmunity, cancer, HIV infection, and other disease similar states. Thus, where there is an increase in a pathologic state, and a corresponding involvement of lymphocytes and mononuclear phagocytes in the combat of such pathologic state, the amount of HLE on the plasma membranes of the lymphocytes and mononuclear phagocytes that can be detected shall diminish. In order to accurately and reliable quantitate HLE on the plasma membranes of the lymphocytes and mononuclear phagocytes, a test sample containing the lymphocytes and mononuclear phagocytes is initially treated with a first antiserum specific for CD4 receptors on the plasma membrane or with a second antiserum specific for chemokine receptors on the plasma membrane. Once the CD4 or chemokine receptors have been rendered non-reactive (competitive) relative to the HLE receptors (also "binding sites") on the plasma membrane, the test sample is contacted with an immunoreagent specific for interation with one or more of the HLE receptors on the plasma membranes of the lymphocytes and mononuclear phagocytes. The immunoreagent forms a complex with the HLE binding sites and produces a characteristic physical change in the lymphocytes and mononuclear phagocytes that can be monitored by any one of a number of standard techniques, (e.g., confocal laser scanning microscopy and flow cytometry). Where the immunoreagent is labeled with a reporter or indicator molecule, the measurement of the complex formed with the lymphocytes and mononuclear phagocytes can be performed by any technique that can concentrate and isolate a detectable signal from such reporter or indicator molecule, (e.g., immunochromatographic analysis, radial partition immunoassay, and microparticle capture immunoassay). In each of the latter analytical systems, the analyte of interest is concentrated within a delimited area of a solid phase and the reporter or indicator molecule measured either directly (by measurement of fluorescence), or measured as function of a discernible change in the delimited area resulting from the interaction of the label (e.g. enzyme) with an additional reagent that results in the production of a chromophore or flourophore.

The quantitative measurement of the HLE on the plasma membranes of lymphocytes and mononuclear phagocytes, indirectly correlates with the progression of the disease and, conversely, directly correlates with the effectiveness of an applied therapy in arresting, or reversal, of its progression.

DESCRIPTION OF THE INVENTION INCLUDING PREFERRED EMBODIMENTS

It has recently been discovered by the inventor that HLE is physically co-localized with CD4 and chemokine receptors on the plasma membrane of lymphocytes and mononuclear phagocytes. This discovery has now made possible for cell-surface density of HLE to be quantitated using antibodies with specificity for HLE. Moreover, because of the physical proximity of HLE with CD4 and chemokine receptors, the order of ligation of these receptors altered detectable cell-surface densities. Specifically, when cells were first interacted with anti-CD4 and second with anti-HLE and anti-chemokine receptor, the cell-surface densities of HLE were quantitative and correlated with other related measures of HLE activity. In contrast, when cells were first interacted with anti-HLE and second with anti-CD4 and anti-chemokine receptor, HLE detection was negligible.

Application of this novel inventive step will allow determination of disease progression in relevant pathologic states resulting from microbial organisms, transplantation, autoimmunity, cancer, HIV infection, and many other disease states. The method of this invention is particularly well-suited for monitoring the progression of disease in seropositive HIV individuals that experience an Aids Related Condition (also herein "ARC Individuals"), and, in individuals that have Acquire Immune Deficiency Syndrome (AIDS) (also "AIDS Individuals"). Moreover, the method of this invention is suitable as an adjunctive procedure to the administration of one or more therapeutic agents—specifically, as means of measurement the effectiveness of such agents, or adjustment in the dosage of such agents in the treatment of ARC and/or AIDS Individuals.

The HLE on the plasma Membrane of lymphocytes and mononuclear phagocytes is fairly well characterized. Thus, the epitopes characteristic of receptor structure, and their availability for accessible binding to an immunoreagent (e.g. antibody mimic), is simply a matter of choice. In one of the preferred embodiments of this invention, the immunoreagent suitable for use in the method of this invention is capable of immunochemical interaction with at least one of the catalytic triad of the HLE membrane surface proteins and the lipid interactive amino acids of the HLE membrane surface proteins. This catalytic triad of HLE (domain 1) is composed of amino acids His (41), Asp (88), and Ser (173). Lipid-interactive amino acids of the HLE (domain 2) is composed of amino acids Phe (170), Ala (187), and Arg (191); and, these amino acids are proximal to the catalytictriad. The HLE specific immunoreagent for use in the diagnostic test method of this invention, thus, comprises binding proteins which interact with one or more of the characteristic domains of membrane surface HLE. In this interaction, the immunocomplex formed between the lymphocytes and mononuclear phagocytes and the immunoreagent specific for HLE on the plasma membranes of cells have a characteristic signature that can be monitored as function of a change in one of more the physical properties of the lymphocytes and mononuclear phagocytes resulting from such interaction, or as function of the "label" or "labels" associated with the immunoreagent.

The CD4 and chemokine receptors on the plasma membrane of lymphocytes and mononuclear phagocytes are also well-characterized, and anti-sera for each of these receptors can be prepared utilizing available techniques and procedures. More specifically, a peptide antagonist suitable for use in preparation of anti-sera is prepared by an iterative process of mutagenesis, expression, chromatographic selection, and amplification. In this process, a gene encoding a potential binding domain corresponding to CD4 and chemokine receptors, respectively, is separately obtained by random mutagenesis of a limited number of predetermined codons, and such gene fused to a genetic element-which causes the resulting chimeric expression product to be displayed on the outer surface of a virus (e.g. a filamentous phage) or a cell. Chromatographic selection is then used to identify viruses or cells whose genome includes a fused gene coded for the protein which is bound to the chromatographic target. The foregoing technique for preparation of the peptide antagonists of this invention is more fully described in Ladner, et al. U.S. Pat. No. 5,571,698, which is herein incorporated by reference in its entirety. These peptides can then be conjugated to a suitable carrier and thereafter used in the method of this invention to block each of the CD4 and chemokine receptors on the plasma membranes of the lymphocytes and mononuclear phagocytes.

In one of the preferred embodiments of this invention, the analysis of a sample of biological fluid containing this immunocomplex is performed by well-known optical scanning techniques (e.g., flow cytometry, laser excited confocal fluorescence scanner microscopy, and modifications thereof). The techniques and equipment suitable for flow cytometry suitable for use in this invention are disclosed in U.S. Pat. No. 6,232,125, which is herein incorporated by reference in its entirety. The techniques and equipment suitable for laser excited confocal fluorescence scanner microscopy suitable for use in this invention are disclosed in U.S. Pat. No. 5,891,738, which is herein incorporated by reference in its entirety.

In another of the preferred embodiments of this invention, the sample of biological fluid containing this immunocomplex is immobilized by physical entrapment within a solid phase, or pre-reacted with an microparticle, the resulting ensemble isolated within a solid phase. The solid phase generally comprise a bibulous material/solid phase (e.g. nitrocellulose or polysulphone synthetic membrane, or a fiberglass) that has been pre-treated within a delimited area thereof with a second binding material specific for second epitope of the cellular component of the immunocomplex, so as to concentrate the immunocomplex within the delimited area of the solid phase. The techniques and equipment suitable for analysis of the HLE density of the plasma membrane of lymphocytes and mononuclear phagocytes within various solid phase test environments are disclosed in U.S. Pat. Nos. 4,703,017; 4,517,288; 5,591,645, & 5,073,484, which are herein incorporated by reference in its entirety.

In the solid phase embodiment of the method of the invention, the immunoreagent typically includes a "label" in the nature of a fluorescent ("reporter") molecule or a radioactive isotope; or an enzyme that is specific for interaction with a chromogenic substrate. In the case of a fluorescent molecule or a radioactive isotope, the cells of the biological fluid sample are capable of direct detection by excitation of the flourophore (in the case of a fluorescent label) or monitoring the emissions of the isotopic label. Alternatively, where the label is in the form of an enzyme, the application of a chromogenic substrate produces a discernible change in the solid phase that can be monitored. In each instance, the amount of immunoreagent associated with the cellular analytes in the immunocomplex is measured, and such measurement compared to a standard curve to provide an indication of the change in surface density of Human Leukocyte Elastase (HLE) associated with plasma membranes of the immunocomplex.

It is, of course, appreciated that all biological samples of leukocytes shall test positive for Human Leukocyte Elastase (HLE) associated with plasma membranes. Thus, the test method of this invention can be biased, relative to sensitivity, to only report a positive test for Human Leukocyte Elastase (HLE) associated with plasma membranes where the HLE surface density exceeds an arbitrary limit (e.g. basal or normal level). Thus, where the individual tested has a normal or elevated amount of Human Leukocyte Elastase (HLE) associated with his plasma membranes, a positive test result will suffice; the test result being semi-quantitative because of the reported amount exceeds the test threshold (basal) value.

In each instance, the measurement of HLE plasma membrane density, when compared to some basal level for an individual, or for a population of individuals similarly infected, provides a barometer showing the relative disease state; and, the response of the disease state to an applied therapy, or to specific dosage levels of an applied therapy.

The Examples which follow further define, describe and illustrate one or more of the preferred embodiments of this invention. Parts and percentages appearing in such Examples are by weight unless otherwise indicated. Procedures, techniques and equipment utilized in the preparation and evaluation of the compositions of this invention are in accordance in standard techniques and procedures unless specified otherwise.

EXAMPLES

The quantitation of cell-surface HLE, in accordance with the method of this invention, is based upon the order of ligation of antibodies specific for HLE, CD4, and chemokine receptors on the plasma membrane of the lymphocytes and mononuclear phagocytes contained in test samples.

The HLE receptors on the plasma membrane of lymphocytes and mononuclear phagocytes are fairly well characterized. Thus, the epitopes characteristic of receptor structure, and their availability for accessible binding to an immunoreagent (e.g. antibody mimic), is simply a matter of choice. In one of the preferred embodiments of this invention, the immunoreagent suitable for use in the method of this invention is capable of immunochemical interaction with at least one of the catalytic triad of the HLE membrane surface proteins and the lipid interactive amino acids of the HLE membrane surface proteins. This catalytic triad of HLE (domain 1) is composed of amino acids His (41), Asp (88), and Ser (173). Lipid-interactive amino acids of the HFLE (domain 2) is composed of amino acids Phe (170), Ala (187), and Arg (191); and, these amino acids are proximal to the catalytic triad. Similarly, the CD4 and chemokine receptors on the plasma membrane of lymphocytes and mononuclear phagocytes are also well-characterized.

More specifically, a peptide antagonist suitable for use in preparation of an immunoreagent and/or anti-sera is prepared by an iterative process of mutagenesis, expression, chromatographic selection, and amplification. In this process, a gene encoding a potential binding domain corresponding to HLE, CD4 and chemokine receptors, respectively, is separately obtained by random mutagenesis of a limited number of predetermined codons, and such gene fused to a genetic element which causes the resulting chimeric expression product to be displayed on the outer surface of a virus (e.g. a filamentous phage) or a cell. Chromatographic selection is then used to identify viruses or cells whose genome includes a fused gene coded for the protein which is bound to the chromatographic target. The foregoing technique for preparation of the peptide antagonists of this invention is more fully described in Ladner, et al. U.S. Pat. No. 5,571,698, which is herein incorporated by reference in its entirety.

These peptides can then be conjugated to a suitable carrier and thereafter used in the method of this invention to prepare an immunoreagent specific for interaction with HLE receptors, or, anti-sera to block each of the CD4 and chemokine receptors on the plasma membranes of the lymphocytes and mononuclear phagocytes.

The HLE specific immunoreagent for use in the diagnostic test method of this invention, thus, comprises binding proteins which interact with one or more of the characteristic domains of membrane surface HLE. In this interaction, the immunocomplex formed between the lymphocytes and mononuclear phagocytes and the immunoreagent specific for HLE on the plasma membranes of cells have a characteristic signature that can be, monitored as function of a change in one of more the physical properties of the lymphocytes and mononuclear phagocytes resulting from such interaction, or as function of the "label" or "labels" associated with the immunoreagent.

Interaction of cells with anti-HLE, in the absence of prior interaction using anti-CD4 or anti-chemokine receptors, is poorly quantitative for cell surface HLE density.

In a further embodiment and in addition to the use of detection of HLE for differential diagnosis and staging of myelogenous disorders as previously noted for individuals that experience an AIDS Related Condition (ARC) and individuals that have Acquired Immune Deficiency Syndrome, (AIDS) the present inventive method is also provides a novel tool for staging leukemia and lymphomas.

While the role of proteolytic enzyme elastase in motility and proliferation of leukemic human AML cells is currently unknown, it has been reported that there is a correlation between abnormal high levers of elastase in the blood of AML patients and the number of leukemic blast cells in the circulation. In AML cells, it has been observed that cell surface elastase were regulated by chemokine SDF-1. In vitro inhibition of elastase prevented SDF-1 induced cell polarization, podia formantion and reduced migration of human AML cells as well as their adhesion. Elastase inhibition also significantly impaired in vivo homing of most human AML cells in the BM of transplanted NOD/SCIDB2m(null) mice. Moreover, in vitro proliferation of AML cells was elastase-dependent. In contrast, treatment with elastase inhibitor enhanced the prolifieration rate of human cord blood CD34(+) cells, including primative CD34(+)/38(−) cells and their in vivo homing. Finally, NOD/SCID mice previously engrafted with human AML cells and treated with elastase inhibitor had significantly reduced egress of leukemic cells into the circulation. Taken together the data demonstrates that human AML cells constitutively secrete and express SDF-1 dependent cell surface elastase, which regulates their migration and proliferation.

Leukemia and lymphomas arise from hematopoietic progenitor cells that become arrested at inappropriate stages of development. Identifying the stage of development of presence or absence of certain cell surface markers is commonly used for this purpose.

Evidence suggests a principal role for HLE during hematopoiesis. Both negative and positive transcriptional elements have been found to restrict expression of HLE to early differentiation stages of myeloid and lymphoid bone marrow cells. Further, biosynthesis and processing of HLE has been shown to produce a single molecular form which is targeted only for secretion early in ontogeny and only for granule compartmentalization later in ontogeny. Thus, HLE is a useful cell surface marker for staging leukemia and lymphomas and a monoclonal HLE-reactive antibody NP57 has been shown to be useful for discriminating and staging myeloid leukemias and lymphomas by microscopic methods. The unique demonstration by this invention that HLE may be detected by flow cytometry on the cell surface of lymphocytes and cells of lymphoid origin provides a novel tool for staging leukemias and lymphomas.

Thus, in a similar manner as set forth in the examples the measurement of HLE plasma membrane density when compared to some basic level for an individual, or for a population of individuals, provides a barometer showing the relation disease state or an applied therapy or a specific dosage level of an applied therapy.

What is claimed is:

1. A method for monitoring the progression and pathological phenomena of leukemia or lymphomas in a subject, said method comprising:
   A. Preparing a test sample which comprises lymphocytes and mononuclear phagocytes;
   B. Blocking CD4 or chemokine receptors on the plasma membranes of lymphocytes and mononuclear phagocytes in said test sample by contacting;
   C. Contacting said plasma membranes of said lymphocytes and mononuclear phagocytes with an immunoreagent specific for interaction with HLE on said plasma membranes, so as to form an immunocomplex;
   D. Monitoring the test sample for the characteristic physical change in the lymphocytes or phagocytes resulting from the immunocomplex; and
   E. Relating the immunocomplex to HLE density, where a change in HLE density corresponds to the progression and pathological phenomenona of leukemia or lymphomas in a subject.

2. The method of claim 1, wherein said immunocomplex is further reacted with another material to produce an indicator species indicative of the presence of the immunocomplex.

3. The method of claim 1, wherein said immunocomplex is monitored directly by confocal laser scanning microscopy and flow cytometry.

4. The method of claim 1, wherein said immunoreagent is labeled with a reporter or indicator molecule capable of producing a detectable signal that can be correlated with HLE density on said plasma membranes.

5. The method of claim 4, wherein the immunocomplex is monitored by isolation with a solid phase and said reporter or indicator molecule is measured by immunochromatographic analysis, radial partition immunoassay, or microparticle capture immunoassay.

6. The method of claim 5, wherein said reporter or indicator molecule comprises a fluorescent material or a material discernible in the visible spectrum.

7. The method of claim 1, wherein the immunoreagent comprises an antibody, specific for interaction with a binding site on said plasma membrane HLE.

* * * * *

UNITED STATES PATENT AND TRADEMARK OFFICE
CERTIFICATE OF CORRECTION

| | | |
|---|---|---|
| PATENT NO. | : 7,833,735 B2 | Page 1 of 1 |
| APPLICATION NO. | : 11/452028 | |
| DATED | : November 16, 2010 | |
| INVENTOR(S) | : Cynthia L. Bristow | |

It is certified that error appears in the above-identified patent and that said Letters Patent is hereby corrected as shown below:

On the Title page please remove the Assignee line.

Signed and Sealed this
First Day of March, 2011

David J. Kappos
*Director of the United States Patent and Trademark Office*